| United States Patent [19] | [11] Patent Number: 4,899,000 |
| Stauffer | [45] Date of Patent: Feb. 6, 1990 |

[54] PRODUCTION OF ALLYL CHLORIDE

[76] Inventor: John E. Stauffer, 6 Pecksland Rd., Greenwich, Conn. 06831

[21] Appl. No.: 303,498

[22] Filed: Jan. 27, 1989

[51] Int. Cl.[4] .................... C07C 17/02; C07C 17/34; C07C 17/15

[52] U.S. Cl. .................................. 570/222; 570/220; 570/224; 570/225; 570/223; 570/231; 570/234

[58] Field of Search ............... 570/222, 220, 223, 224, 570/225, 231, 234

[56] References Cited

U.S. PATENT DOCUMENTS 2,447,410  8/1948  Hampel ............................... 570/220
3,449,450  6/1969  Bohl et al. ........................... 570/220

Primary Examiner—Howard T. Mars

Attorney, Agent, or Firm—Krass & Young

[57] ABSTRACT

A process is provided for the production of allyl chloride from three carbon atom hydrocarbons (propane and/or propylene) using hydrogen chloride or hydrogen chloride/chlorine mixtures as the chlorinating agent. The process includes reaction steps operated in tandem in separate zones first comprising the reaction of perchloroethylene with hydrogen chloride and oxygen in the presence of an oxychlorination catalyst to give hexachloroethane and water, second comprising the vapor phase reaction of hexachloroethane with propane/propylene feedstock to produce allyl chloride, perchloroethylene, and hydrogen chloride, and third isolating the products of the second step and repeating the first step using as starting materials the thus isolated perchloroethylene and hydrogen chloride.

11 Claims, 1 Drawing Sheet

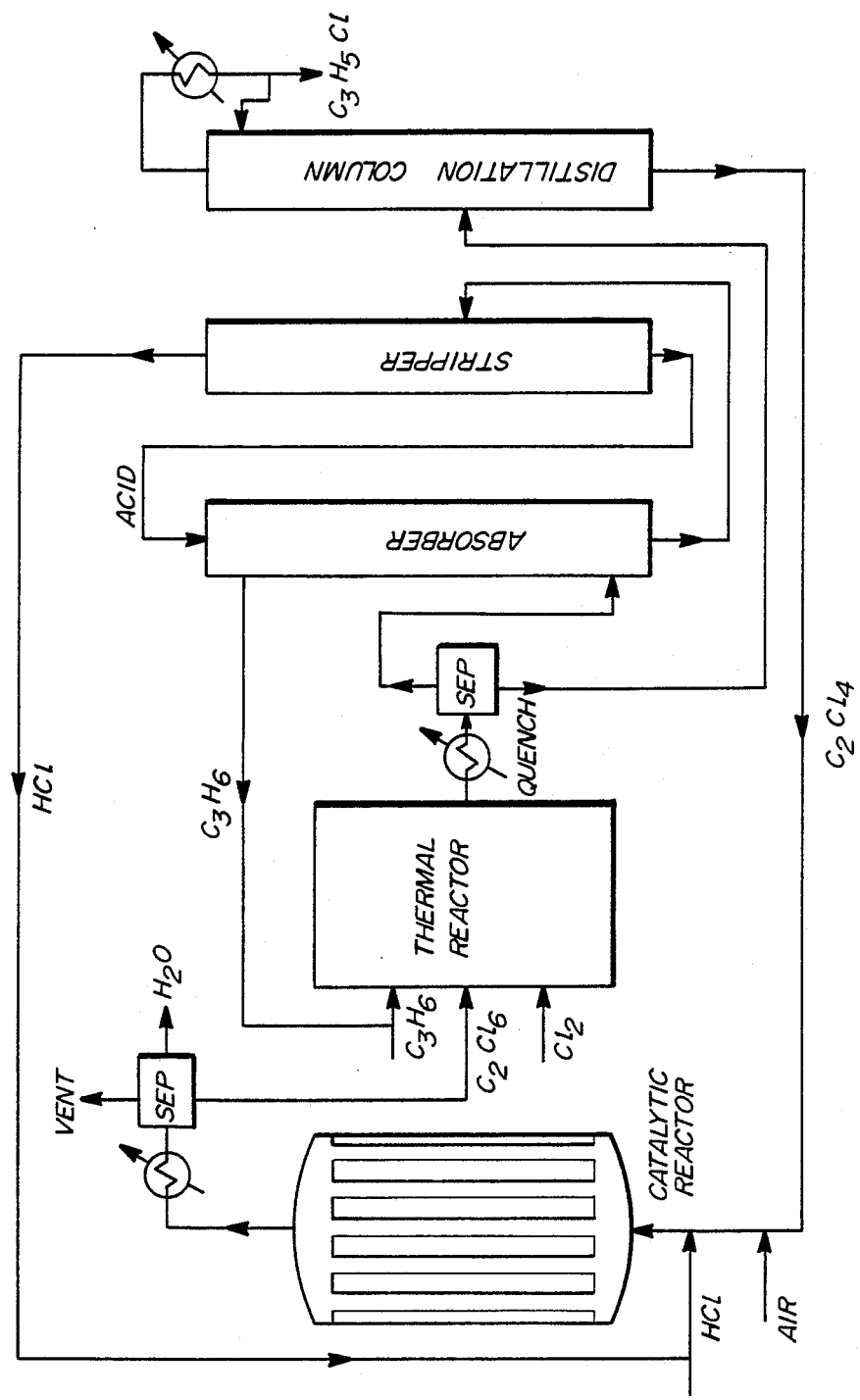

PRODUCTION OF ALLYL CHLORIDE

FIELD OF THE INVENTION

This invention relates to a novel method of producing allyl chloride ($CH_2=CHCH_2Cl$) from hydrocarbons containing three carbon atoms, i.e., propane and propylene, using hydrogen chloride or chlorine as the chlorinating agent. An important feature of the process is that any proportion of hydrogen chloride to chlorine can be used and the net production of hydrogen chloride can be avoided. A further advantage of the process is that high yields of allyl chloride can be obtained based on the hydrocarbon and the chlorine values used.

DESCRIPTION OF THE PRIOR ART

Historically, allyl chloride has been made by the addition chlorination of propylene with chlorine followed by the pyrolysis of 1,2-dichloropropane at high temperatures. The resulting product mix from the dehydrochlorination reaction consists of about 55 to 70 percent allyl chloride and approximately 30 to 40 percent 1-chloropropene. Because of the relatively low yield of allyl chloride this process is not used industrially at the present time.

The newer method of producing allyl chloride involves the high-temperature substitution chlorination of propylene with chlorine to produce the product directly in one step. High yields of allyl chloride, up to 96 percent, have been reported for the reaction. Minor quantities of 2-chloropropene-1 and 1-chloropropene-1 are obtained.

The above method of making allyl chloride commercially has several disadvantages. First, it requires chlorine as the chlorinating agent. This raw material, which is produced by an electrochemical process, has been vulnerable to the escalating cost of electric power. Second, less than half of the chlorine consumed is used to produce allyl chloride. The rest of the chlorine is wasted, mostly as byproduct hydrogen chloride.

The object of the present invention, therefore, is to be able to produce allyl chloride by substituting hydrogen chloride for all or part of the chlorine requirements. Thereby dependence on an expensive raw material, which on occasion has been in short supply, is avoided.

A further object of the present invention is the production of allyl chloride without producing byproduct hydrogen chloride. Added flexibility and improved economics thus can be realized.

Still another object is to manufacture allyl chloride in high yields from propane and/or propylene. Several benefits accrue from this result. The consumption of hydrocarbon is minimized. Processing costs of purifying the product are reduced. Finally, the disposal of unwanted and environmentally-damaging byproduct chlorohydrocarbons can be simplified.

BRIEF DESCRIPTION OF THE DRAWINGS

FIG. 1 is a diagrammatic representation of a preferred means for operating the present chlorination method. A shell and tube catalytic reactor is illustrated in series with a thermal reactor with means for separating allyl chloride and for isolating and recycling hydrogen chloride and perchloroethylene to the catalytic reactor.

SUMMARY AND DETAILED DESCRIPTION

The invention, in one preferred embodiment, concerns a process of the chlorination of a hydrocarbon containing three carbon atoms using hydrogen chloride as a source of chlorine. The process includes reaction steps operated in tandem in separate reaction zones; first, comprising the reaction of perchloroethylene with hydrogen chloride and oxygen in the presence of an oxychlorination catalyst to give hexachloroethane and water, and second, comprising the vapor phase reaction of hexachloroethane with a hydrocarbon containing three carbon atoms to produce allyl chloride as the principal product along with hydrogen chloride and perchloroethylene.

The invention, in another preferred embodiment, concerns a process for the chlorination of a hydrocarbon containing three carbon atoms using hydrogen chloride as a source of chlorine, said process including reaction steps operated in tandem; first subjecting perchloroethylene to oxychlorination with hydrogen chloride and oxygen in the presence of an oxychlorination catalyst to give reaction products consisting essentially of hexachloroethane and water; second, isolating and reacting said hexachloroethane with a hydrocarbon containing three carbon atoms in the vapor phase to produce a product stream comprising predominantly allyl chloride, perchloroethylene and hydrogen chloride; and third, isolating said products of the second step, and repeating the first step using as starting materials the perchloroethylene and hydrogen chloride thus isolated whereby chlorination using regenerated hexachloroethane is accomplished; the process being operated with total utilization of hydrogen chloride and net production of hydrogen chloride and hexachloroethane being avoided.

Problems encountered by the conventional methods are circumvented by the method of the present invention. In the present method, according to a preferred embodiment, two separate reactions are carried out in tandem, as indicated. First, perchloroethylene is reacted with hydrogen chloride and air or oxygen to produce hexachloroethane and water. In the second reaction the hexachloroethane is reacted with a hydrocarbon containing three carbon atoms, i.e. propane, propylene or any proportion of these compounds, to give the desired allyl chloride plus hydrogen chloride. The latter is recycled to the first reaction so that there is no net production of hydrogen chloride.

The reactions in the present invention may be illustrated by the following equations using propylene as the hydrocarbon feedstock:

1. $CCl_2=CCl_2 + 2HCl + \tfrac{1}{2} O_2 \xrightarrow{cat.} CCl_3CCl_3 + H_2O$ 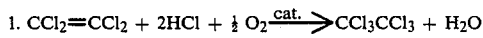

2a. $CCl_3CCl_3 + C_3H_6 \xrightarrow{\Delta}$ 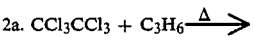

$CCl_2=CCl_2 + CH_2=CHCH_2Cl + HCl$ 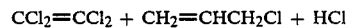

Therefore the net reaction is:

3. $C_3H_6 + HCl + \tfrac{1}{2}O_2 \rightarrow CH_2=CHCH_2Cl + H_2O$ 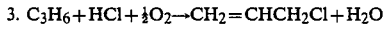

If, in a preferred embodiment, chlorine is added in the second step, the following reaction will occur:

2b. $Cl_2 + C_3H_6 \xrightarrow{\Delta} CH_2=CHCH_2Cl + HCl$

Also, when using propane, the following reaction will occur:

2c. $CCl_3CCl_3 + Cl_2 + C_3H_8 \rightarrow CCl_2=CCl_2 + CH_2=CHCH_2Cl + 3HCl$

The first reaction, in which perchloroethylene is oxychlorinated to hexachloroethane employing an oxychlorination catalyst, may typically be carried out in a molten salt reactor, fluidized bed reactor or in a shell and tube reactor. Such reactor designs assist in the control of the reaction temperature. This temperature is maintained preferably in the range from about 200° C. to about 375° C. The catalyst of choice is copper chloride which may be deposited on an inert support. This is the well-known Deacon catalyst which has been used in experimental processes to produce chlorine from hydrogen chloride and air. Various salts may be mixed with the copper chloride in order to promote its effectiveness, e.g. potassium chloride, ferric chloride, and lead chloride.

The second reaction is conducted in the vapor phase at an elevated temperature preferably in the range from about 400° C. to about 700° C. The probable mechanism by which propylene is chlorinated in this temperature range is a series of free radical reactions. In the event that insufficient hydrogen chloride is available to produce the required hexachloroethane, chlorine can be added to supplement the hexachloroethane. Thus, various predetermined proportions of hydrogen chloride and chlorine, depending on requirements, can be used in the overall process.

As a feature of the invention, temperature control of the second reaction is facilitated when using hexachloroethane instead of chlorine as the chlorinating agent. Substitution chlorination, such as the formation of allyl chloride from propylene and chlorine, releases considerable heat. By contrast, dissociation reactions, such as the instant decomposition of hexachloroethane to perchloroethylene and chlorine, absorb a substantial quantity of heat. Thus, according to the present invention, when these two reactions, substitution chlorination and dissociation, are connducted in an intimate manner, the heat requirements can be closely balanced.

Operation of the process is illustrated in the attached drawing. Air, hydrogen chloride and perchloroethylene are fed to the shell tube reactor which contains the copper chloride catalyst. The effluent is cooled sufficiently to condense the liquids. The inert gases are vented to a scrubber while a separator decants the water from the chlorinated organics. After being dried, hexachloroethane dissolved in unreacted perchloroethylene is pumped to the thermal reactor where it chlorinates propylene. The hot vapors from the reactor are quenched, and the hydrogen chloride is separated from hydrocarbons by absorption in an acid stream for recycle to the catalytic reactor. Unreacted hydrocarbon is recycled to the thermal reactor. The chlorinated organic compounds are fractionated in a distillation column. Allyl chloride is removed overhead and the higher boiling perchloroethylene is recovered in the still bottoms and returned to the oxychlorination step.

Although the process seems rather straightforward, successful operation depends of the strict adherence to the following rules:

1. Hexachloroethane produced via oxychlorination must be isolated from all impurities with the exception of perchloroethylene before being fed to the thermal reactor. This separation is necessary to avoid the formation of byproducts and the loss of hydrogen chloride efficiency. The thermal reactor must be kept anhydrous or above the dew point to prevent severe corrosion problems. All oxygen has to be excluded from the thermal reactor to avoid burning and the formation of water.

2. Hydrogen chloride in the thermal reactor product stream, before being recycled to the oxychlorination reactor, must be freed of all hydrocarbons to prevent combustion reactions and to avoid pollution problems caused by their escape in the vent gases.

3. Perchloroethylene that is reformed in the thermal reactor must be isolated from the product stream before being recycled to the oxychlorination reactor. Any saturated hydrocarbons which are fed to the oxychlorination reactor will partially burn. Unsaturated hydrocarbons, other than perchloroethylene, will be chlorinated in the oxychlorination reactor and eventually lead to unwanted byproducts.

The allyl chloride produced by the method of the present invention is a valuable item of commerce. It is an intermediate in the production of allyl alcohol, epichlorohydrin, and synthetic glycerol. End use markets include pharmaceuticals, resins, plastics and food products. Recent market research data indicate that epichlorohydrin accounts for 5.7 percent of chlorine consumption in the United States and is the second fastest growing outlet for chlorine.

The embodiments of the invention in which exclusive property or privilege is claimed are defined as follows:

I claim:

1. A process for the production of allyl chloride using hydrogen chloride as a source of chlorine, said process including reaction steps operated in tandem;

first subjecting perchloroethylene to oxychlorination with hydrogen chloride and oxygen in the presence of an oxychlorination catalyst to give reaction products consisting essentially of hexachloroethane and water;

second, isolating and reacting said hexachloroethane with a hydrocarbon containing three carbon atoms and optionally added chlorine, in the vapor phase to produce a product stream comprising predominantly allyl chloride, perchloroethylene and hydrogen chloride; and third, isolating said products of the second step and repeating the first step using as starting materials the perchloroethylene and hydrogen chloride thus isolated whereby chlorination using regenerated hexachloroethane is accomplished, the process being operated with total utilization of hydrogen chloride and net production of hydrogen chloride and hexachloroethane is avoided.

2. A process according to claim 1, wherein the hydrocarbon containing three carbon atoms that is reacted in the second step comprises propane.

3. A process according to claim 1, wherein the hydrocarbon containing three carbon atoms that is reacted in the second step comprises propylene.

4. A process according to claim 1, in which chlorine is added such that the second step comprises the reaction of chlorine with a hydrocarbon containing three carbon atoms to produce allyl chloride and hydrogen chloride.

5. A process according to claim 1, in which the catalyst in step 1 comprises copper chloride.

6. A process according to claim 5, where the catalyst comprises an admixture of copper chloride with one or more salts selected from the group consisting of potassium chloride, ferric chloride, and lead chloride.

7. A process according to claim 1, in which the oxychlorination reaction with perchloroethylene is carried out at temperatures in the range from about 200° C. to about 375° C.

8. A process according to claim 1, in which the vapor phase reaction is carried out at temperatures in the range from about 400° C. to about 700° C.

9. A process according to claim 1, wherein the step of isolating the perchloroethylene from the product stream includes a distillation operation.

10. A process according to claim 1, wherein the step of isolating the hydrogen chloride from hydrocarbons includes an absorption operation.

11. A process according to claim 1, wherein the step of isolating the hexachloroethane includes a drying operation.

* * * * *